United States Patent
Lind et al.

Patent Number: 5,722,423
Date of Patent: Mar. 3, 1998

[54] TISSUE REMOVING DEVICE

[75] Inventors: Stuart Lind, Minneapolis; Daniel Dostal, Eden Prairie; John Skaaland, Hopkins, all of Minn.

[73] Assignee: Annex Medical, Inc., Eden Prairie, Minn.

[21] Appl. No.: 366,822

[22] Filed: Dec. 30, 1994

[51] Int. Cl.⁶ ................................................. A61B 10/00
[52] U.S. Cl. ........................................ 128/756; 128/757
[58] Field of Search .............................. 128/756, 757, 128/758, 759

[56] References Cited

U.S. PATENT DOCUMENTS

| | | | |
|---|---|---|---|
| 2,328,998 | 9/1943 | Radford | 51/185 |
| 2,388,867 | 11/1945 | Peterson | 300/21 |
| 2,465,396 | 3/1949 | Peterson et al. | 15/206 |
| 2,609,642 | 9/1952 | Peterson | 51/190 |
| 2,763,104 | 9/1956 | Lindenborg | 51/190 |
| 2,846,827 | 8/1958 | Peterson | 51/193 |
| 2,908,117 | 10/1959 | Hall | 51/193 |
| 2,955,592 | 10/1960 | MacLean | 128/2 |
| 2,984,053 | 5/1961 | Peterson | 51/193 |
| 3,521,620 | 7/1970 | Cook | 128/2.05 |
| 3,613,664 | 10/1971 | Willson et al. | 128/2 R |
| 3,799,151 | 3/1974 | Fukaumi et al. | 128/6 |
| 4,108,162 | 8/1978 | Chikashige et al. | 128/2 B |
| 4,235,244 | 11/1980 | Abele et al. | 128/749 |
| 4,682,606 | 7/1987 | DeCaprio | 128/754 |
| 4,776,346 | 10/1988 | Beraha et al. | 128/754 |
| 4,785,826 | 11/1988 | Ward | 128/754 |
| 4,936,312 | 6/1990 | Tsukagoshi | 128/749 |
| 4,955,862 | 9/1990 | Sepetka | 604/164 |
| 4,961,430 | 10/1990 | Sheahon | 128/754 |
| 4,966,162 | 10/1990 | Wang | 128/750 |
| 4,986,279 | 1/1991 | O'Neill | 128/754 |
| 4,991,588 | 2/1991 | Pflueger et al. | 128/662 |
| 5,146,928 | 9/1992 | Esser | 128/756 |
| 5,272,845 | 12/1993 | Burkley | 51/364 |

*Primary Examiner*—Max Hindenburg
*Assistant Examiner*—Pamela L. Wingood
*Attorney, Agent, or Firm*—Scully, Scott, Murphy & Presser

[57] ABSTRACT

A tissue removing device and brush construction, and more particularly, a cytology brush construction which is intended to be utilized in conjunction with a specimen sampling device for the collection of microbiological biopsy specimen from a body cavity. The brush construction is attained by the provision of at least one initially flat element which may have at least one or opposing longitudinal outer edges in either a wavy-linear configuration, rectilinear form, or which may incorporate a multiplicity of closely spaced, parallel slits cut in from at least one longitudinal edge so as to leave a central longitudinal connecting web in the element. The flat element, upon being twisted into a helical configuration or by being interposed between a pair of wires or superimposed wire strands and which are then twisted, will exhibit the desired configuration and properties of a tissue removing device or cytology brush, with the elimination of the multiplicity of separate discrete bristles or filaments heretofore employed. Also disclosed as a brush structure is the use of a flattened plastic tube or the like having a plurality of slits cut into it from both edges thereof and which, upon being deformed into a helical brush-shape, will provide for an improved and enhanced collection of tissue specimen material.

10 Claims, 3 Drawing Sheets

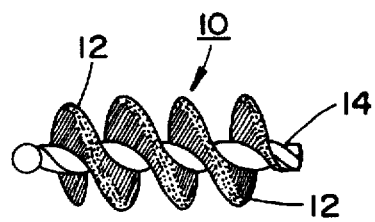
FIG. 1
(PRIOR ART)
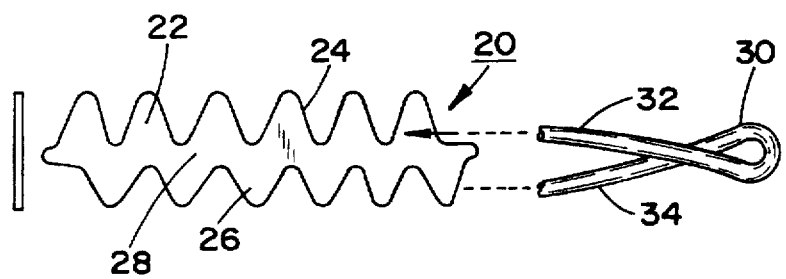 
FIG.3  FIG.2  FIG.4
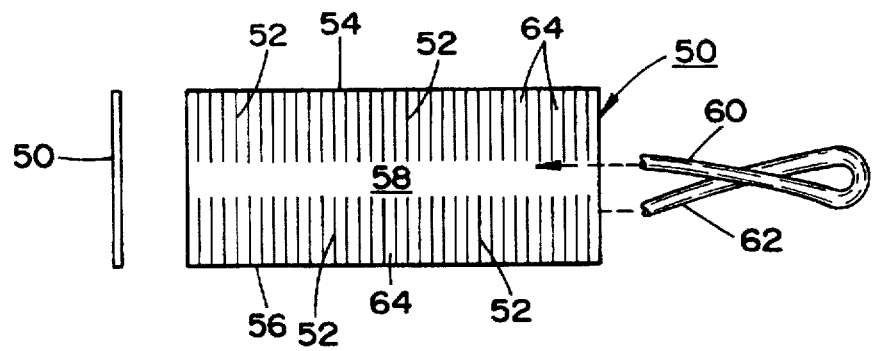 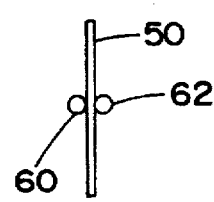
FIG.7  FIG.6  FIG.8
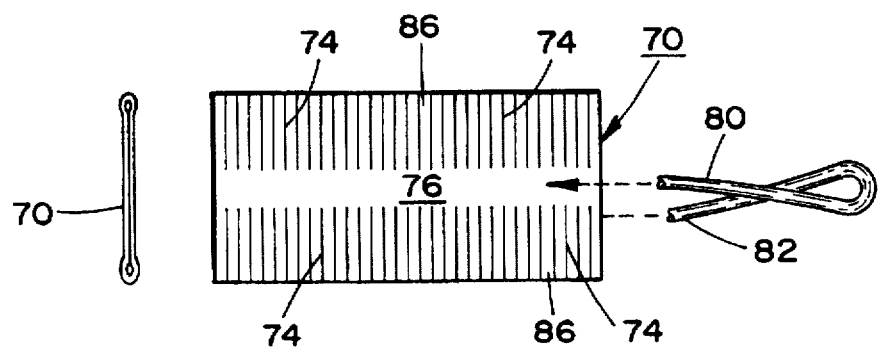 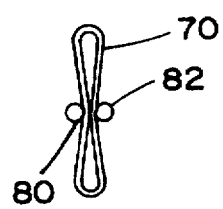
FIG.10  FIG.9  FIG.11

TISSUE REMOVING DEVICE

BACKGROUND OF THE INVENTION

1. Field of the Invention

The present invention relates to a tissue removing device, and more particularly, pertains to a tissue removing scraper, rasp or cytology brush construction which is intended to be utilized in conjunction with a specimen sampling device for the collection of microbiological biopsy or tissue specimen from a body cavity. Moreover, the tissue removing device or cytology brush is especially adapted for, but not limited to, the brushing and retrieving of microbiological biopsy and tissue specimen from areas of the pulmonary or gastrointestinal tracts of a patient which are ordinarily difficult to reach. Other applications may include utilization for cardiovascular plaque removal; uses in urology, obstetrics/gynecology, neurological; and even in connection with the employment of the inventive device as endoscope cleaning brushes. The tissue removing device can also be conceptually utilized in various industrial aspects, such as for the cleaning/treatment of delicate tools and instruments. Pursuant to a specific aspect of the invention, the cytology brush construction is of a simple and inexpensive, yet sturdy and reliably operable nature, and is constituted from a minimum number of components which will avoid encountering any loss of brush bristles during use in the implementation of invasive biopsy procedures, while concurrently enhancing the versatility and range of applicability of the cytology brush. The inexpensive and simple construction of the cytology brush also renders the latter readily disposable in a highly economical manner after only a single use.

Biopsy specimen sampling and tissue removing devices employing cytology brushes for the collecting of microbiological specimen from body cavities are extensively employed in the medical technology, particularly in conjunction with their use in endoscopic procedures, and are of widely varied types which, however, are concurrently either of generally complicated constructions necessitating the manufacture and assembly of cytology brushes or similar structures consisting of numerous generally expensively produced components or; alternatively, may be of such simple constructions as to lack the sophistication and strength to enable them to be satisfactorily applied for their intended purposes. This, in particular, pertains to the various types of cytology brushes currently employed for the collection of microbiological biopsy specimen from the body cavities of patients through the insertion of the brushes into endoscopes and in the brushing and obtention of microbiological biopsy samples from pulmonary or gastrointestinal tracts, and other potentially biopsied regions of the body cavities from which tissues are to be obtained. In general, presently utilized cytology brushes, which are utilized for the obtaining of microbiological biopsy specimen, incorporate a flexible operating cable or wire which is actuated from a first or proximal end in order to effectuate longitudinal and rotational movement of the wire within a flexible sheath, for instance, such as a sheath constituted from plastic tubing which is insertable into the biopsy channel of an endoscope, and at the end of the sheath extending into the body cavity of a patient has a second or distal end of the wire equipped with a cytology brush structure. Ordinarily, such a cytology brush includes a multiplicity of discrete or separate bristles, each generally constituted from nylon or suitable substantially rigid but resiliently flexible plastic material, wherein the radially outer ends of the bristles, when the cytology brush is extended outwardly beyond a distal end of the sheath into the body cavity, are adapted to brush against and obtain microbiological biopsy specimen from specified areas or regions in the body cavity of the patient. Thereafter, the cytology brush with the microbiological biopsy specimen entrained in or located on the bristles is withdrawn from the distal end of the plastic sheath, and the entire sampling device retracted from the body cavity through the endoscope.

Although this type of brush construction is generally satisfactory in enabling the cytology brush bristles to contact the particular internal body portions or organs being biopsied and from which the microbiological biopsy specimen or tissue samples are to be obtained, the structure of the brush bristles being constituted from a multiplicity of separate components which are clampingly retained in a helically-coiled position between twisted strands of the flexible wire, raises the concern of the possibility that some of the bristles may become loosened and detached while in the body cavity of the patient, and resultingly leading to potential physical hazards and infection to the patient, and attendant legal liability to the medical practitioner and facility.

Although such occurrences are extremely rare, nevertheless, there is still a risk factor involved in the potential separation and loss of cytology brush bristles during the effectuation of the specimen sampling procedure, resulting in physical harm to the patient and exposure to possible lawsuits by the medical personnel and/or facilities with attendant financial liabilities and adverse publicity in the medical profession and in the eyes of the public.

2. Discussion of the Prior Art

At this time, numerous types of constructions for specimen sampling devices employed in the collection of microbiological biopsy specimen from body cavities, and which incorporate cytology brushes, are known in the medical profession.

Abele et al. U.S. Pat. No. 4,235,244 discloses a microbiological specimen sampling device which includes a cytology brush mounted at the distal end of an operating wire which is adapted to be longitudinally displaced within a tubular plastic member, and which has a second outer sleeve mounted over the plastic member enabling the cytology brush to be extended some distance beyond and outwardly the leading or distal end which is adapted to be inserted through an endoscope into a body cavity so as to enable the brush bristles to collect microbiological biopsy specimen samples from the body cavity of a patient.

The bristles of the brush are constituted of a large number or multiplicity of separate constituents, consisting of a material such as nylon or a suitable plastic, and which are retained in place and twisted into helical brush configuration by being clampingly supported between a pair of twisted wire strands forming a central cable support structure.

Similarly, Esser U.S. Pat. No. 5,146,928 discloses a sampling device for collecting microbiological biopsy specimen in which the bristles of the cytology brush are constituted of a large number of separate and discrete brush bristle elements which are held in position between two wires which are twisted so as to impart a helical brush configuration to the collective brush bristles.

McLean U.S. Pat. No. 2,955,592 discloses a diagnostic instrument for collecting cell samples including a brush adapted to be inserted into a body cavity, and which brush includes a plurality of discrete brush bristle elements mounted so as to form a helical brush structure.

A similar construction is also disclosed in Tsukagashi U.S. Pat. No. 4,936,312 wherein a body cavity inserting instrument for medical treatment includes a brush consisting of a large number of discrete bristle elements attached to an operating wire enclosed within a helically-coiled outer sheathing.

Chikashiga et al. U.S. Pat. No. 4,108,162 discloses a twisted brush for collecting cells or biological tissue samples from internal body passages in which a large number of discrete hairy fibers extend clampingly supported between twisted wire strands so as to form a helical brush structure.

This type of construction may also be ascertained in Peterson et al. U.S. Pat. No. 2,465,396 in which large numbers of separate fibers are clampingly engaged between wire strands or a bent wire, which wire is or the strands of which are then twisted to impart a helically-coiled brush configuration to the collective bristles.

Similar features in the formation of brushes from multiplicities of separate collective bristle fibers may also be ascertained from Peterson U.S. Pat. No. 2,984,053; Hall U.S. Pat. No. 2,908,117; Peterson U.S. Pat. No. 2,609,642; and Lindenborg U.S. Pat. No. 2,763,104.

All of these brush structures, at least some of which are adapted to be employed for retrieving biopsy specimen purposes, pertain to discrete or large numbers of brush bristles which are clampingly fastened in position by means of a central wire or cable strands which are twisted in a manner so as to produce a brush construction; for example, in the shape of a helically-curved cytotogy brush.

However, none of the patent publications described hereinabove disclose the formation of tissue removing devices and cytology brush structures which are constituted from a minimum or limited number of components, and in which the brush bristle portions forming the biopsy sample obtaining or tissue scraping or abrading surfaces are essentially constructed from either single or unitary initially plate-like components clampingly fastened to a central support wire or cable; or alternatively, constituted of only a few plate-like parts which in selective embodiments are clampingly engaged by a central supporting wire or cable and which is twisted so as to form a helically-shaped brush structure consisting of only a few components and eliminating the use of large numbers of separate brush bristles or filaments.

SUMMARY OF THE INVENTION

In essence, the inventive tissue removing device or cytology brush construction is attained, pursuant to one embodiment, by the provision of an initially flat element which may have opposing longitudinal outer edges in either a wavy-linear configuration or which may incorporate a multiplicity of closely spaced, parallel slits cut in from each or from at least one longitudinal edge so as to leave a central longitudinal connecting web in the element; and which element, upon being twisted into a helical configuration by being interposed between a pair of wires or superimposed wire strands and which are then twisted, or by simply being twisted by itself, will exhibit the desired configuration and properties of a cytology brush, with the elimination of the multiplicity of separate discrete bristles or filaments heretofore employed.

In accordance with the inventive device in a cytology brush concept, brush bristle-forming structure, which may be constituted of only a few components depending upon the various sizes and intended uses for the brush, there may be employed a diverse selection of materials, such as different plastics and metals which are physiologically compatible with the intended medical applications thereof, for producing the brush bristles.

Moreover, the inventive tissue removing device also facilitates the obtaining of improved and superior cutting edges for removing microbiological biopsy sample specimen or tissue material and can be designed so as to vary from fine or broaching action to extremely soft abrading capabilities.

Also contemplated as a brush structure is the use of a flattened plastic tube or the like having a plurality of slits cut into it from both edges thereof and which, upon being deformed into a helical brush-shape, will provide for an improved and enhanced collection of biopsy specimen sample material during the implementation of a biopsy upon passing the brush across the biopsied area in the body cavity.

Pursuant to another aspect of the invention, the wavy-linear configuration of the tissue removing structure of the device upon being formed into a helical shape may also be utilized to facilitate a rasping action through the edges simulating a helical scraper or rasp for scraping larger samples of biological biopsy material or tissue and plaque from the internal body cavity of a patient.

Accordingly, it is an object of the present invention to provide an improved tissue removing device in the form of a cytology brush construction for the use in specimen sampling devices adapted for the collection of microbiological biopsy specimen from a body cavity, wherein the brush construction is constituted of a minimum number of operative components.

A more specific object of the present invention is to provide a tissue removing construction in which brush bristles or scraping edges are produced from a unitary plate member which is shaped into a helical brush or scraper configuration by being clamped by a twisted central support wire cable.

Yet another object of the present invention is to provide a simple tissue removing device, preferably in the form of a cytology brush construction, in which the brush bristles are formed from a single plate element having a multiplicity of closely spaced slits cut into opposing longitudinal edges thereof along the longitudinal axis of the plate, and with a central wire positioned along the central axis of the plate being twisted so as to cause the plate to assume a helical brush configuration with the slits causing the outer edges to simulate brush bristle filaments.

A further object of the present invention is to provide a flattened tube structure having a plurality of closely spaced slits cut into the tube from opposite flattened edges thereof so as to form a helical brush construction upon being twisted between a pair of cooperating wire cables clampingly engaged along the central axis of the tube structure.

A still further object of the present invention is to provide a tissue removing device construction in which a plate member is twisted between cable or wire strands and end members engage the latter so as to form a generally helical wavy-linear brush structure of integral construction providing a scraping or rasping edge surface for the retrieval of biological biopsy specimen or tissue from a body cavity.

A yet further object of the invention is to provide a tissue removing device of the type described in which a pair of wavy-linear plate members are adapted to be positioned on opposite sides of a central elongate support and twisted thereabout so as to form a helical brush structure of a construction having wavy-linear outer edge surfaces forming a rasp for enabling scraping and retrieving biological biopsy sample, tissue or plaque material from a body cavity.

BRIEF DESCRIPTION OF THE DRAWINGS

The foregoing objects and other features and advantages of the present invention may now be more readily ascertained from the following detailed description of exemplary embodiments of tissue removing and cytology brush structures, taken in conjunction with the accompanying drawings; in which:

FIG. 1 illustrates a typical biopsy specimen brush for collecting biological biopsy specimen constructed pursuant to the prior art;

FIG. 2 illustrates a plan view of a first embodiment of a plate element for producing a tissue removing device pursuant to the invention prior to being twisted into a helical configuration;

FIG. 3 illustrates an end view of the plate element of FIG. 2;

FIG. 4 illustrates an end view of the opposite end of the plate element of FIG. 2 showing the wire strands for forming the brush structure;

FIG. 6 illustrates a plan view of another embodiment of a plate element for forming a tissue removing brush construction pursuant to the invention prior to being deformed into a helical brush retained between wire strands;

FIG. 7 illustrates an end view of the plate element of FIG. 6;

FIG. 8 illustrates an end view of the opposite end of the plate element of FIG. 6 showing the wire strands for forming the brush structure;

FIG. 9 illustrates a plan view of a further embodiment of a tissue removing device, such as a helical cytology brush construction pursuant to the invention produced from a flattened tubular member;

FIG. 10 illustrates an end view of the plate element of FIG. 9;

FIG. 11 illustrates an end view of the flattened tubular member of FIG. 9 showing the wire strands for forming the brush structure;

DETAILED DESCRIPTION OF PREFERRED EMBODIMENTS

Figure 5:
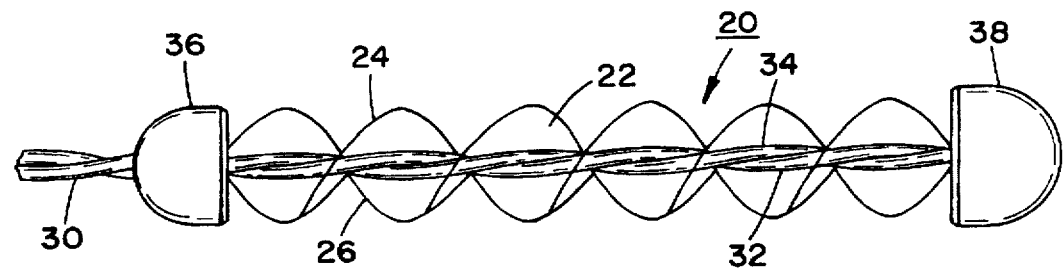
FIG. 5 illustrates a tissue removing device in the form of a cytology brush construction similar to FIG. 2 in the final helical brush configuration thereof.

Referring now in more specific detail to the drawings, FIG. 1 illustrates a prior art cytology brush construction 10 utilized for the collecting of cells, and which is of a typical structure as commonly used in the medical technology.

In connection with the prior art cell collecting brush construction 10, the brush is constituted of a multiplicity of individual bristles 12 which are centrally clampingly engaged by a twisted wire or cable member 14 forming a root portion so as to cause the bristle fibers to assume a helical brush configuration. Although the individual bristles 12, as illustrated in the drawing, are firmly and clampingly engaged at their central portions between the intertwined strands of the center wire cable 14, there still exists the possibility that one or more of the individual strands of the brush bristles 12 may not be properly secured and, during use of the brush, may conceivably be dislodged in the body cavity of a patient having the brush inserted therein. This may lead to serious consequences, with the patient sustaining potentially grievous physical injury and mental trauma, and also to legal and financial liability for the medical practitioner and the medical facility employing the brush.

In order to essentially obviate the foregoing potential risks and to also concurrently provide an inexpensively produced tissue removing device, which in various embodiments is in the form of a cytology brush which may be readily employed for the collection and obtention of microbiological biopsy specimen from the body cavity of a patient, pursuant to the invention in lieu of employing a multiplicity of individual fiber strands to form the bristles for the brush, these have been replaced by a tissue removing device or cytology brush structure in which the brush bristle components or tissue removing components are constituted from either a unitary construction or from only a few elements rather than from a multiplicity of individual and separate bristles. Moreover, the inventive tissue removing device or cytology brush structure enables the effectuation of a greater degree of control over the physical characteristics or property of the brush by merely substituting different kinds of materials for the brush bristle portion and/or various tissue removing configurations, as desired for specific physical applications.

Referring specifically to FIGS. 2 through 4 of the drawings, illustrating one embodiment of the inventive tissue removing construction, the tissue scraping brush or rasp 20 is formed initially from a generally flat plate member 22 which has longitudinally opposite wavy-linear edge portions 24 and 26 arranged in complementary orientations so as to provide a central connecting web 28 extending along the longitudinal length of the plate member 22.

A flexible wire 30 which may be bent so as to have one strand 32 extending along one side of the web 28 and a second strand 34 extending on the opposite side thereof in superimposed relationship, as illustrated in FIG. 4 of the drawings, provide the actuating wire or cable for the tissue scraping brush or rasp 20. The wire is twisted, similar to that illustrated in the prior art of FIG. 1, so as to produce a helical brush-like configuration as shown in FIG. 5 of the drawings. Hereby, the length of the tissue removing portion 20 is defined by end members or stops 36 and 38 and in which the portion may have an outer diameter of approximately 0.08 to 0.09 inches. The entire portion 20 is adapted to extend into and project from a plastic sheath 40 forming an insert extendable through a suitable endoscope (not shown).

The plate member 22 for forming the tissue removing or potential cytology brush structure 20 may be constituted of a suitable plastic material, for example, such as nylon or the like, or a stainless metal, such as a surgical steel having a thickness of preferably about 0.001 to 0.003 inches. When formed into the brush configuration of FIG. 5, the outer diameter of the helical brush formed by the twisted outer edges 24 and 26 may form a relatively sharp cutting or rasping edge enabling the scraping of relatively large amounts of cells or tissue from the body cavity of a patient.

Alternatively, in lieu of the plate member as shown in FIG. 2 of the drawings, referring to FIGS. 6 through 8, an initially flat substantially rectangular plate 50 may have a large number of closely spaced parallel slits 52 formed therein extending from the opposite longitudinal edges 54 and 56 to such an extent as to cause a longitudinal central connecting web 58 to extend from end to end of the plate. As in the previous embodiment, a flexible wire, which may be constituted of suitable surgical steel or the like, has strand portions 60 and 62 thereof located and extending on opposite sides of the central web of the plate 50, and is then twisted in a manner analogous to that illustrated in FIG. 1 of the drawings to provide a helical brush configuration. The slits 52 define therebetween a large number of brush bristles 64 which are of an integral structure in view of the connecting web 58 extending centrally along the longitudinal axis of the plate 50. Accordingly, there are no separate or discrete bristles or filaments which can conceivably loosen from their clamping interconnection with the twisted wire or cable strands 60, 62. As in the previous embodiment, the plate 50 may be constituted of a suitable plastic material, such as nylon or, if desired, depending upon the physical application intended for the tissue removing brush, may be constituted of metal such as a surgical steel. The thickness of the plate member may also be generally within the range of 0.001 to 0.003 inches, and the spacing between the adjacent slits 52 may be dimensioned so as to provide bristle-like filaments 64 therebetween generally analogous to those found in cytological brushes constructed of individual or separate bristles.

Pursuant to a further embodiment as shown in FIGS. 9-11 of the drawings, in lieu of the flat plate shown in FIG. 6, the rectangular member illustrated in FIG. 9 may be constituted of a flattened plastic tube 70 whereby the plurality of slits 74 formed therein is substantially similar to those formed in the embodiment of FIG. 6 of the drawings. The slits 74 extend through both longitudinal edges of the flattened tube 70 so as to provide a central longitudinal connecting web 76 on both sides of the flattened plastic tube. Superimposable in clamping relationship over this longitudinal connecting web are the strands 80 and 82 of a bent flexible wire or cable element, which is then twisted to provide a helical tissue removing or cytology brush construction as in the previous embodiments. In this instance, the use of the flattened plastic tube 70 provides a greater area and size at the outer ends of the thus formed bristle filaments 86 so as to facilitate the assumption and removal of larger quantities of biopsy specimen from the body cavity of a patient.

Figure 12:
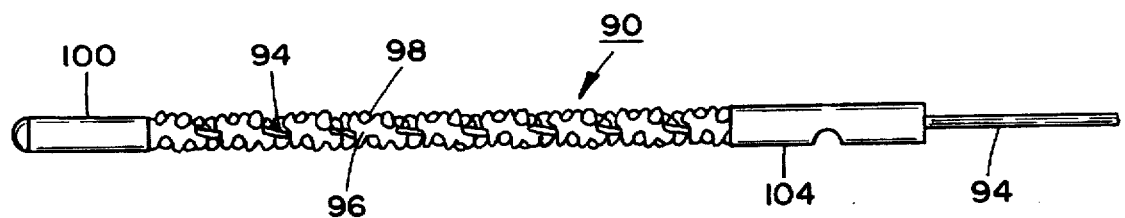
FIG. 12 illustrates a still further embodiment of a tissue removing structure pursuant to the invention.
Figure 13:
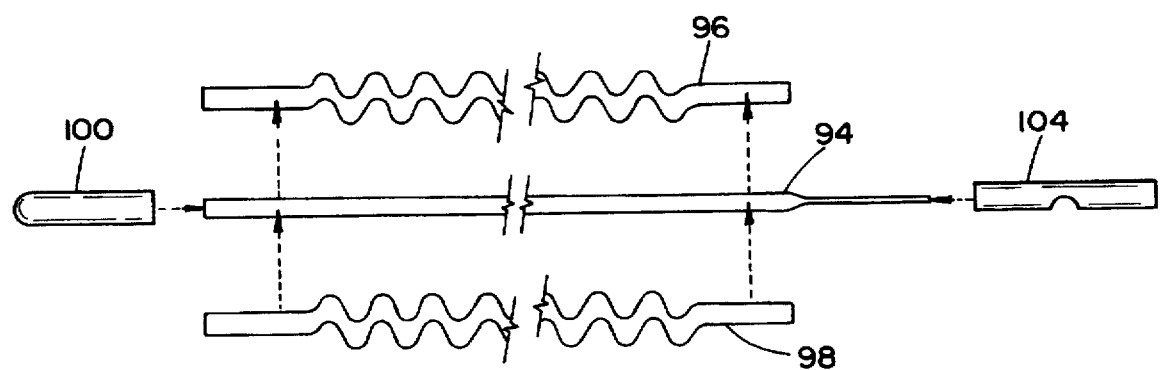
FIG. 13 illustrates the components of the tissue removing structure of FIG. 12 in an exploded view prior to being assembled and formed into the helically-twisted configuration.

Referring to an embodiment of the tissue removing rasp or brush construction 90, as illustrated in FIGS. 12 and 13 of the drawings, in this instance, as shown in FIG. 12, there is provided a relatively hard cutting edge or rasping surface for removing microbiological biopsy samples or tissue from body cavities.

The construction in this instance, as shown in the exploded view of FIG. 13, is such that a central flexible rod member 94 has superimposed on opposite sides thereof wavy-linearly shaped flat plates 96 and 98, and which are then twisted in conjunction with the central rod or wire member 94 so as to provide a helical brush-shaped configuration, as shown in FIG. 12 of the drawings. Thereafter, end stop 100 is superimposed at one end and a further sleeve 104 is superimposed on the other end of the wire member 94 so as to define the length of the brush portion connected to an actuating wire to be; for example, approximately 0.250 to 0.375 inches in length. The thickness of each of the flat plate elements 96, 98 which are twisted about the central rod or wire 94 may also range from about 0.001 to 0.002 inches. This particular embodiment provides a more rigid tissue removing construction which is particularly adapted to impart rasping or tissue cutting action along the outer helical brush edges thereof.

Figure 14:
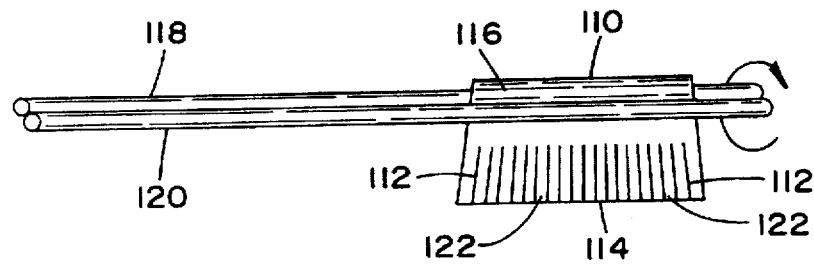
FIG. 14 illustrates a tissue removing device similar to that of FIG. 6, prior to being twisted into a helical configuration, showing a modified plate element.

Referring to the embodiment of the tissue removing device illustrated in FIG. 14 of the drawings, this is quite similar to that illustrated in the embodiment of FIGS. 6 through 8. However, in this instance the initially flat plate 110 has a large number of closely spaced parallel slits 112 extending radially inwardly only from a single longitudinal edge 114. The opposite, unslitted plate portion 116 may be contacted on opposite sides thereof by strands 118 and 120 of a flexible wire which, as in the embodiment of FIGS. 6 though 8, is then twisted to provide a helical tissue removing or brush structure. The slits 112 define therebetween a large number of bristles 122, and the plate member 110 may be of a thickness and material analogous to that of the embodiment of FIGS. 6 though 8 of the drawings.

Figure 15:
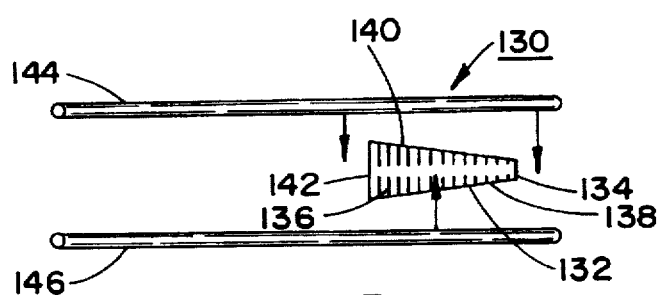
FIG. 15 illustrates a further tissue removing device similar to that of FIG. 14, showing another shape of plate element.

Similarly, with respect to the embodiment of the tissue removing device 130 shown in FIG. 15 of the drawings, this is also similar to that of FIGS. 6 through 8. However, in this instance the plate element 132 is of a frusto-conical configuration having a narrower end 134 towards the tip portion of the device, and with slits 136 extending inwardly from the opposite converging edges 138 and 140 so as to leave a central connecting web 142. This web 142 may be engaged by strands 144 and 146 of a flexible wire which is then twisted in a manner analogous to that referred to hereinabove with respect to the embodiment of FIGS. 6 through 8, with the primary distinction being that the brush has a tapered helical configuration towards the leading ends 134 thereof.

Figure 16:
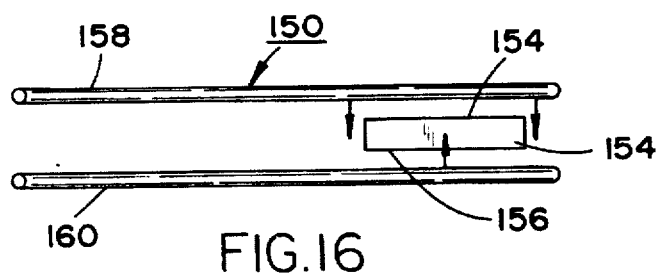
FIG. 16 illustrates a tissue removing device similar to that of FIG. 2, shown in an exploded view, prior to assembly of the components thereof.

With respect to the embodiment 150 of FIG. 16 of the drawings, this is substantially analogous to that shown in FIG. 2; however, the plate member 152 is an essentially rectilinear configuration having parallel longitudinal edges 154, 156 rather than the wavy-linear form of the plate member 28 as shown in FIG. 2. Again, the plate member 152 is twisted between the wire strands 158, 160 so as to be imparted a helical configuration.

Figure 17:
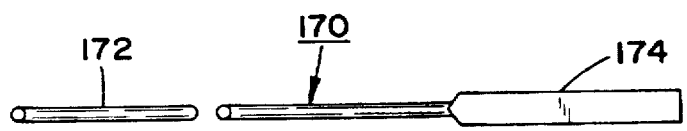
FIG. 17 illustrates another embodiment of a tissue removing device, prior to being twisted into the final configuration thereof, as being constituted from a single component.
Figure 18:
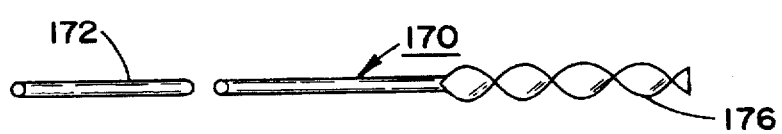
FIG. 18 illustrates the device of FIG. 17 shown in its helically-twisted configuration.

With respect to the embodiment of FIGS. 17 and 18, in this instance the tissue removing device 170 is constituted of essentially a single component. Hereby, a generally flexible wire 172 has the leading end 174 flattened so as to provide a generally elongate plate-shaped end portion which, as shown in FIG. 18, is then twisted to a helical configuration 176 so as to form a helically-twisted rasp having the edges thereof producing tissue-removing structure.

Figure 19:
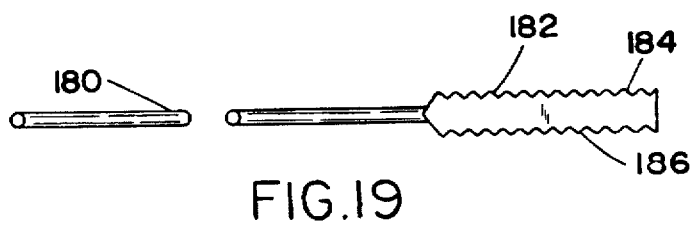
FIG. 19 illustrates another embodiment of a tissue removing device similar to that of FIG. 17.

FIG. 19 is similar to the embodiment of FIGS. 17 and 18; however, the wire 180 has the flattened end portion 182 provided with serrated or teeth-shaped configurations at both opposite longitudinal edges 184, 186. This structure in which teeth or teeth-forming shapes are ground into the opposite edges provide a somewhat more "bite" to the component in removing tissue.

From the foregoing, the advantages attained by the present invention in the elimination of the numerous separate bristle filaments which are currently employed in the forming of tissue removing devices; for instance, such as cytology brushes, resides in that there is no potential loss of bristles from the brush or device during use thereof; there may be as few as one or two components or only as many as four or five depending upon the size and type of the tissue removing device or brush being constructed; while a large variety of materials, such as various plastics or metals, may be employed in producing the device; and better cutting edges can be attained, extending from fine or broach action to a very soft brushing effect. Furthermore, when employing a flattened plastic tube 70, such as in the embodiment of FIG. 9 of the drawings, it is also possible to attain an improved collection of biopsy materials without appreciably changing the construction of the tissue removing device or cytotogy brush.

From the foregoing, it quite clearly becomes evident that the present invention is adapted to provide versatile and inexpensively produced tissue removing devices and microbiological cytology brush constructions which readily eliminate the disadvantages and drawbacks potentially encountered in the utilization of brushes possessing large numbers of individual bristles clampingly engaged between twisted cable wires.

Moreover, in view of the inexpensive inventive tissue removing or cytology brush structure, which is particularly adapted for use in conjunction with endoscopic instruments and which facilitates imparting a considerable versatility in the characteristics and properties to the brush construction, the entire brush assembly may be readily disposable in an economic manner after only a single use. This aspect of inexpensive disposability is highly desirable in view of the considerable risks to patients being subjected through the employment of reused cytology brushes to potential exposure to serious and even life-threatening infection with the AIDS virus (Acquired Immunity Deficiency Syndrome) or Hepatitis-B viruses notwithstanding the sterilizing of such devices and cytology brushes, inasmuch as even current procedures in the sterilizing or autoclaving of such cytology brushes may not be always adequate to destroy viruses and may even possibly raise doubts as to the efficacy of this sterilizing solutions commonly employed.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. A brush construction for the collection and obtention of microbiological specimen from a body cavity, said brush construction comprising:
    a) at least two elongate plate-shaped elements having at least one edge adapted for specimen obtention; and
    b) an elongate flexible member connected to said at least two plate-shaped elements, said elongate flexible member being twisted along the longitudinal extent of said elongate flexible member so as to impart a helically-spiraled configuration to said brush construction, whereby said at least one longitudinally extending edge forms the outer extremities of said brush structure.

2. A brush construction as claimed in claim 1, wherein end stops are mounted on said flexible member so as to define the axial length of said brush configuration.

3. A brush construction as claimed in claim 1, wherein the longitudinally extending edges of each of said plate-shaped elements are wavy-linear so as to define a helical rasping edge extending along said brush structure.

4. A brush construction as claimed in claim 1, wherein said elongate flexible member comprises a stainless steel wire.

5. A brush construction as claimed in claim 1, wherein said plate-shaped elements are each constituted from a plastic material.

6. A brush construction as claimed in claim 5, wherein said plastic material comprises nylon.

7. A brush construction as claimed in claim 1, wherein said plate-shaped elements are each constituted from a metallic material.

8. A brush construction as claimed in claim 7, wherein said metallic material comprises a stainless steel alloy.

9. A brush construction as claimed in claim 1, wherein each said plate-shaped element has a thickness of about 0.001 to 0.003 inch.

10. A brush construction as claimed in claim 1, wherein said brush construction comprises a cytology brush.

* * * * *